United States Patent [19]
Herold et al.

[11] Patent Number: 4,792,692
[45] Date of Patent: Dec. 20, 1988

[54] DENTAL IRRADIATION APPARATUS

[75] Inventors: Wolf-Dietrich Herold; Karlfried Lucks, both of Seefeld, Fed. Rep. of Germany

[73] Assignee: Espe Stiftung & Co. Produktions-Und Vertriebs KG, Seefeld, Fed. Rep. of Germany

[21] Appl. No.: 33,370

[22] Filed: Apr. 2, 1987

[30] Foreign Application Priority Data

Apr. 3, 1986 [DE] Fed. Rep. of Germany ....... 3611132

[51] Int. Cl.$^4$ ............................................. G21K 1/06
[52] U.S. Cl. ........................... 250/504 H; 250/504 R; 350/96.1
[58] Field of Search ....................... 250/504 H, 504 R; 350/96.1

[56]  References Cited
U.S. PATENT DOCUMENTS

| | | | |
|---|---|---|---|
| 3,101,411 | 8/1963 | Richards | 250/504 R |
| 3,868,513 | 2/1975 | Gonser | 250/504 H |
| 4,233,493 | 11/1980 | Nath | 250/504 R |
| 4,298,806 | 11/1981 | Herold | 250/504 H |

FOREIGN PATENT DOCUMENTS 2507601 9/1976 Fed. Rep. of Germany .
8504351 5/1985 Fed. Rep. of Germany .

*Primary Examiner*—Bruce C. Anderson
*Assistant Examiner*—Jack I. Berman
*Attorney, Agent, or Firm*—Foley & Lardner, Schwartz, Jeffery, Schwaab, Mack, Blumenthal & Evans

[57] ABSTRACT

An irradiation apparatus for curing photopolymerizable dental fillings in situ comprises a lamp 10 for producing a convergent light beam with a convergence angle $\alpha E$ smaller than about 30° with respect to the optical axis, and an optical wave guide 15 having an entrance surface 14 disposed in the light beam and an exit surface 16. The wave guide 15 is conical with a diameter decreasing from the entrance surface 14 to the exit surface 16 and has a refractive index of approximately $\sqrt{2}$. At the exit surface 16, radiation of constant density and high intensity is produced within a substantially semi-spherical lobe, so that even such dental parts which are difficult to access can be irradiated and penetrated with high intensity radiation.

11 Claims, 1 Drawing Sheet

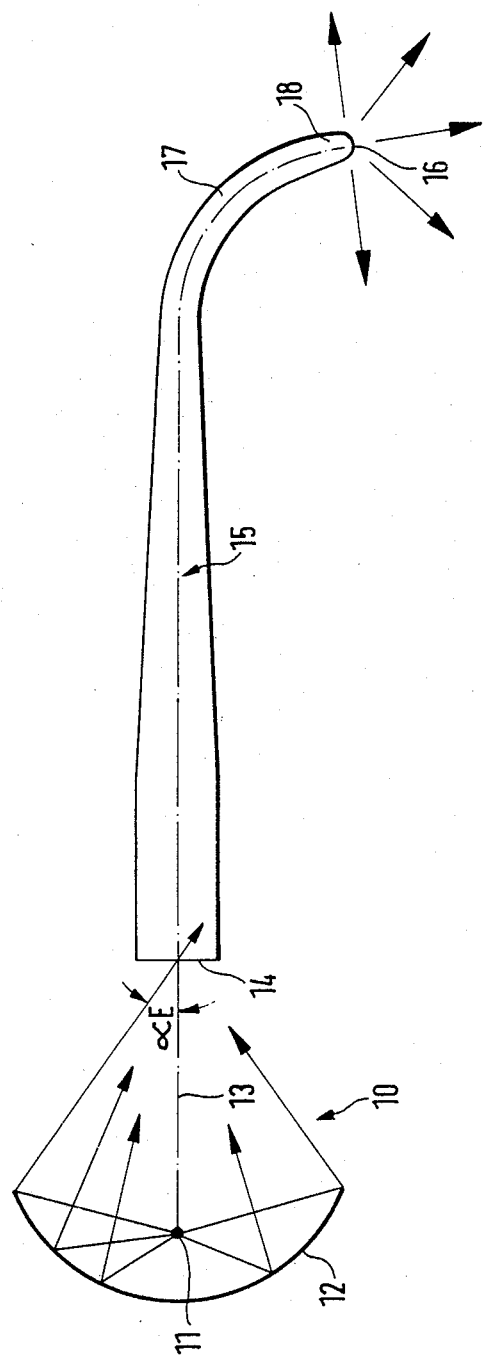

DENTAL IRRADIATION APPARATUS

DESCRIPTION

A dental irradiation apparatus comprising a lamp for producing a convergent beam of radiation and an optical waveguide having an entrance surface disposed wtthin the beam and an exit surface adapted to be oriented with respect to a location to be irradiated is known from German Offenlegungsschrift No. 2,507,601. The optical waveguide provided in that apparatus has a constant diameter over its substantial length which, in practice, is about 8 mm, and the waveguide is bent near its exit end by an angle of about 60° and has at its tip a conical portion of decreasing diameter. A similar irradiation apparatus without such a tapering tip portion is disclosed in U.S Pat. No. 4,298,806. The known apparatus permit photopolymerizable tooth fillings to be cured in situ by occlusal irradiation.

Radiation-settable materials are known to shrink during polymerization at a degree which increases with the polymerization temperature. Since the filling material always shrinks towards the source of radiation, there is a tendency for the material to lift off the bottom and/or the sides of the cavity in case of a purely occlusal irradiation.

This tendency may be counteracted by irradiating the filling material disposed in the cavity from the bottom or sides of the cavity. To this end, it is necessary either to penetrate the tooth itself with radiation of a correspondingly high intensity or, in case of multi-facial fillings, to apply the radiation totthe filling material from an interdentalapical position Either way of irradiation is practically impossible with the conventional optical waveguides It is an object of the present invention to devise a dental irradiation apparatus with an optical waveguide which enaables irradiation of individual dental areas in situ from any desired direction at an intensity which is sufficient to cure photopolymerizable fillings starting from the cavity walls.

To meet with this object, the dental irradiation apparatus according to the present invention includes an optical waveguide having an entrance surface disposed in a convergent beam of radiation produced by a lamp and an exit surface adapted to be oriented with respect to the location to be irradiated, the angle of convergence being smaller than approximately 30° with respect to the optical axis defined by the lamp, and the waveguide being conically shaped over a substantial part of its length with a diameter decreasing from the entrance surface to the exit surfcce.

On account of the angle at which the radiation enters the optical waveguide and also because of the taper of the waveguide and the increased radiation divergence resulting therefrom, a substantially semi-spherical lobe of approximately constant radiation intensity is achieved at the exit surface of the waveguide; as a consequence, the end of the waveguide may be placed in practically any desired orientation with respect to the location to be irradiated while the material is still reliably cured. This is of great significance in view of the limited space, particularly in interdental areas or in case of curing distal molar fillings. Because of the constant radiation density, there is no danger of the filling material being exposed to excessive radiation intensity and thus overheated, inspite of large irradiance.

If transparent interdental wedges are used, a very large amount of radiation may be coupled into the small axial end face of the wedge which radiation is emitted by the lateral wedge surfaces to cure filling material starting from a proximal-apical region.

While the entrance surface may have a sufficient cross-section to receive a corresponding amount of irradiance, the exit surface of the optical waveguide according to the present invention is comparatively small, thereby permitting direct irradiation of interdental areas which cnnnot be reached by conventional waveguides. Due to the decrease in diameter, high intensity radiation is obtained at the exit surface which penetrates even relatively thick dentin layers. In the interior of the tooth, starting from the cavity walls, an intensive curing of the filling material is achieved, which strongly adheres to the tooth wall.

German utility model specification No. 8,504,351 discloses an optical waveguide for a dental irradiation apparatus which has a portion conically tapering from an entrance surface. This portion, however, is followed by a portion increasing in cross-section towards an exit surface which is larger than the entrance surface. This waveguide serves to irradiate larger surfaces with parallel light as uniformly as possible, and it is ipportant in the practical use of this waveguide that the exit surface be placed on the surface to be cured in a substantially flush manner.

In a preferred embodiment of the invention, the material of the waveguide has a refractive index ratio with respect to the invironment of greater than about 1.3, preferably about $\sqrt{2}$. The radiation emitted by the lamp may thus have a great angle of convergence without being totally reflected at the exit surface. A great angle of convergenee of the radiation beam emieted by the lamp is advantageous in that, in case a substantially point-shaped source of radiation is used with an ellipsoidal reflector, the reflector may be comparatively short in the direction of the optical axis, while utilizing a given portion of the overall radiation produced. When the refractive index is about $\sqrt{2}$, a substantially semispherical lobe of radiation is actually achieved at the exit surface. With a smaller refractive index the exit angle also decreases.

In another preferred embodiment of the invention, the ratio of the diameter of the exit surface to that of the entrance surface ranges from about 0.5 to about 0.2 and is preferably about 0.3, with the diameter of the entrance surface being about 10 mm, that of the exit surface about 3 mm, and the length of the waveguide being about 100 mm. With these dimensions, a waveguide is achieved which is easy to handle in practice and which can be used in connection with available lamps and irradiation apparatus, while a reasonable portion of the overall amount of available radiation is utilized.

Preferably, a portion of the waveguide close to its exit surface is bent about an angle of approximately 60 to 90°, preferably 75°. With this shape, even such dental areas which are difficult to access can be sufficiently irradiated. In order to avoid radiation to exit from the peripheral surface of the bent waveguide portion, the diameter of that portion is essentially constant.

In a furteer preferred embodiment of the invention, the exit surface of the waveguide is crowned, and the tapering of the waveguide in a portion immediately before the exit surface is more pronounced than over its remaining length to enable placing the radiation spill closer to fillings in interdental spaces. At the same time, a drop of radiation intensity in the vicinity of an angle of 90° with respect to the optical axis is avoided near the exit surface, as far as possible.

A preferred embodiment of the invention will now be described in detail with reference to the drawing which is a schematic representation of a lamp and an optical waveguide.

The lamp 10 shown in the drawing includes a substantially point-shaped source of radiation 11 disposed at one focus of an ellipsoidal reflector 12. The lamp 10 produces a convergent beam of radiation the angle $\alpha E$ of which measures about 30° with respect to the optical axis 13. At or close to the second focus of the reflector 12, the entrance surface 14 of an optical waveguide 15 is dispoeed. The optical axis of the waveguide 15 at the entrance surface 14 coincides with the optical axis 13 of the reflector 12. The waveguide 15 has a crowned exit surface 16, a bent portion 17 of constant diameter close to the exit surface 16, and a portion 18 having a steeper tapering than exists between the entrance surface 14 and the bent portion 17. The portion 18 is disposed immediately before the exit surface 16.

The optical waveguide 15 has an overall conical shape of circular cross-section with the following dimensions:

| | |
|---|---|
| diameter d1 of the entrance surface 14: | 10 mm |
| diameter d2 of the exit surface 16: | 3 mm |
| length of the waveguide measured along its optical axis: | approx. 100 mm |
| length of the straight portion of the waveguide between the entrance surface 14 and the beginning of the bent portion 17: | approx. 75 mm |
| diameter of the waveguide in the bent portion 17: | 4 mm |
| radius of the center line of the bent portion 17: | 20 mm |
| angle of curvature: | approx. 75° |
| length of the portion 18 of steeper tapering, within which the diameter decreases from 4 mm to 3 mm: | 5 mm |

The waveguide 15 is made of quartz having a refractive index of approximately 1.46, which approximately equals $\sqrt{2}$. The waveguide may be formed as a solid rod or composed of a plurality of discrete radiation conducting fibers. Glass or synthetic material may be used instead of quartz.

Given the above values, a beam of radiation incident on the entrance surface 14 at an angle $\alpha E$ of approximately 22° is transmitted through the waveguide 15 to the exit surface 16 which it hits at the limit angle of total reflection, leaving the exit surface at an angle of 90° with respect to the optical axis. Beams incident on the entrance surface 14 at smaller angles leave the exit surface 16 at correspondingly smaller angles. This results in an overall semi-spherical lobe of radiation from the exit surface 16.

Beams incident on the entrance surface 14 within an angular range of approximately 22° to 30° leave the waveguide laterally before reaching the exit surface 16 substantially within that region in which the diameter is smaller than about 3.6 mm. It is therefore preferable to select the entrance angle $\alpha E$ greater than that value (approximately 22°) at which all radiation is transmitted to the exit surface, thus ensuring that radiation of sufficient intensity is available at the exit surface 16 even under large angles with respect to the optical axis. Since the portion 18 disposed immediately before the exit surface 16 has a steeper tapering than the remaining waveguide, any radiation which does not reach the exit surface 16 will leave the waveguide very shortly before the same, thereby enhancing the useful radiation in case the rod is laterally applied.

If the ratio of the refractive index of the optical waveguide to that of the environment has the above value of $\sqrt{2}$, any beam carried by the waveguide will reach the exit surface 16, and the largest exit angle will be 90°. With a smaller refractive index ratio, the maximum exit angle will be smaller than 90°. If, in this case, the angle of incidence $\alpha E$ is increased, radiation will be emitted from the peripheral wall of the waveguide. If the refractive index ratio is made greater than $\sqrt{2}$ part of the radiation transmitted through the waveguide will be totally reflected at the exit surface 16; while this may be avoided by reducing the angle of incidence $\alpha E$, a corresponding portion of the radiation emitted by the lamp 10 will be lost, or th ellipsoidal reflector 12 must be shaped so that it surrounds the source of radiation 11 more completely with the result that the reflector must have a greater axial length, thereby incressing the overall dimension of the lamp 10.

If the exit surface 16 is made planar, in contrast to the above-described embodiment, it will be seen that the radiation intensity decreases and a dark zone is produced in a range of about 85 to 90° with respect to the optical axis. This dark zone is avoided by the crowned or rounded shape of the exit surface 16.

We claim:
1. A dental irradiation apparatus comprising
   a lamp for producing a convergent beam of radiation having an angle of convergence approximately 30° or less with respect to the optical axis defined by said lamp, and
   an optical waveguide having an entrance surface disposed in said beam and an exit surface adapted to be oriented with respect to a location to be irradiated, the waveguide being conically shaped over a substantial part of its length with a diameter decreasing from said entrance surface to said exit surface.
2. The apparatus of claim 1, wherein the material of the waveguide has a refractive index ratio with respect to the environment of greater than approximately 1.3.
3. The apparatus of claim 2, wherein the refractive index ratio is approximately $\sqrt{2}$.
4. The apparatus of clim 1, wherein the ratio of the diameter of the exit surface to that of the entrance surface of said waveguide is between about 0.5 and about 0.2.
5. The apparatus of claim 4, wherein the said ratio is about 0.3.
6. The apparatus of claim 1, wherein the entrance surface has a diameter of approximately 10 mm, the exit surface has a diameter of approximately 3 mm, and the length of the waveguide is approximately 100 mm.
7. The apparatus of claim 1, wherein a portion of the waveguide near the exit surface is bent about an angle of approximately 60° to 90°.
8. The apparatus of claim 7, wherein said angle is approximately 75°.
9. The apparatus of claim 7, wherein the diameter of the bent portion is substantially uniform.
10. The apparatus of claim 1, wherein the exit surface is rounded.
11. The apparatus of claim 1, wherein a portion of the waveguide immediately adjacent the exit surface has a cone angle greater than that of the other part of the waveguide, the diameter decreasing within adjacent portion to such an extent that radiation exits through the conical peripheral surface of said portion at a distance of up to 20 mm from said exit surface.

* * * * *